US012731674B2

(12) United States Patent
Taubmann et al.

(10) Patent No.: US 12,731,674 B2
(45) Date of Patent: Sep. 8, 2026

(54) METHOD AND CONTROL UNIT FOR CONTROLLING A MEDICAL IMAGING INSTALLATION

(71) Applicant: Siemens Healthineers AG, Forchheim (DE)

(72) Inventors: Oliver Taubmann, Weilersbach (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 221 days.

(21) Appl. No.: 18/476,612

(22) Filed: Sep. 28, 2023

(65) Prior Publication Data

US 2024/0112785 A1 Apr. 4, 2024

(30) Foreign Application Priority Data

Sep. 29, 2022 (EP) .................................... 22198687

(51) Int. Cl.
*G16H 30/20* (2018.01)
*G16H 10/60* (2018.01)
*G16H 30/40* (2018.01)

(52) U.S. Cl.
CPC ............ *G16H 30/40* (2018.01); *G16H 10/60* (2018.01); *G16H 30/20* (2018.01)

(58) Field of Classification Search
CPC ........ G16H 30/40; G16H 10/60; G16H 30/20; G16H 40/60; G06N 3/09; G06N 3/096; G06N 3/084; G06N 3/0985; G06N 3/08; G06N 20/00; A61B 6/54; A61B 6/03; A61B 6/481; A61B 5/055; A61B 6/00; A61B 6/032; A61B 6/545; A61B 8/00
See application file for complete search history.

(56) References Cited

U.S. PATENT DOCUMENTS

2015/0269508 A1* 9/2015 Damboritz ............ G16H 40/20 705/2
2018/0144243 A1* 5/2018 Hsieh ..................... G06F 30/27
2019/0069869 A1 3/2019 Soza et al.
2019/0139271 A1* 5/2019 Tung ..................... G16H 40/63
2020/0097773 A1* 3/2020 Hsieh ..................... G06N 3/084
(Continued)

FOREIGN PATENT DOCUMENTS

EP 3451211 A1 3/2019

OTHER PUBLICATIONS

Kalra A, Chakraborty A, Fine B, Reicher J. Machine Learning for Automation of Radiology Protocols for Quality and Efficiency Improvement. J Am Coll Radiol. 2020;17(9):1149-1158. doi: 10.1016/j.jacr.2020.03.012 (Year: 2020).*
(Continued)

*Primary Examiner* — Joshua B Blanchette
(74) *Attorney, Agent, or Firm* — Harness, Dickey & Pierce, P.L.C.

(57) ABSTRACT

A computer-implemented method for controlling a medical imaging installation, comprises: capturing patient-specific indication data via an interface unit; capturing at least one user-specific and/or facility-specific preference parameter via an interface unit; automatically determining, via an arithmetic unit, a control data record on the basis of the indication data and the preference parameter; and controlling, via the arithmetic unit, the medical imaging installation using the control data record.

12 Claims, 3 Drawing Sheets

(56) References Cited

U.S. PATENT DOCUMENTS

2021/0183055 A1* 6/2021 Rao ........................ G06T 7/0012
2022/0130017 A1* 4/2022 Zhang ................ G01R 33/5611

OTHER PUBLICATIONS

Brown AD, Marotta TR. Using machine learning for sequence-level automated MRI protocol selection in neuroradiology. J Am Med Inform Assoc. 2018;25(5):568-571. doi:10.1093/jamia/ocx125 (Year: 2018).*

* cited by examiner 400
410
420
430
440
$x_1$
$x_2$
$x_3$
$x_i$
$w_1$
$w_2$
$w_3$
$w_i$
$f(\sum x_i w_{i1}) = h_1$
$f(\sum x_i w_{i2}) = h_2$
$f(\sum x_i w_{i3}) = h_3$
$f(\sum x_i w_{ij}) = h_j$
$f(\sum w_{ij} h_i) = o_j$
$o_j$

METHOD AND CONTROL UNIT FOR CONTROLLING A MEDICAL IMAGING INSTALLATION

CROSS-REFERENCE TO RELATED APPLICATION(S)

The present application claims priority under 35 U.S.C. § 119 to European Patent Application No. 22198687.0, filed Sep. 29, 2022, the entire contents of which is incorporated herein by reference.

BACKGROUND

Many steps in a diagnostic imaging and evaluation workflow require manual interaction from the medical personnel. This is effected via a corresponding operating interface at the medical imaging installation and/or at a radiological evaluation station. In order to perform the image data capture, decisions relating to e.g. the scan protocol, the reconstruction parameters and the postprocessing of the generated images must be made and typically entered manually. This process can be simplified and rationalized via automation. The number of required interactions can be reduced in this way. This saves time and reduces the risk of error resulting from undesired variations in the workflows or due to inherent standardization thereof. Use is also routinely made of automated postprocessing solutions for the generated image data in order to assist radiologists during the evaluation. As part of this activity, many different standardized postprocessing results are often generated automatically, this requiring considerable processing power and corresponding time for both the automatic generation and the manual examination, selection and clinical evaluation by the radiologist.

Such approaches have become increasingly relevant with the introduction of photon-counting detector technology, since the detection of the x-radiation via photon-counting x-ray detectors per se involves a larger volume of data and in comparison with conventional x-ray detector technology offers numerous additional options for providing results in the form of (postprocessed) image data due to the spectral information which is also included.

Workflow automation requires knowledge of patient-specific indication information in a format that can be processed by machine. In other words, it must be known why a patient is to undergo medical imaging, since the indication in conjunction with further patient-related factors determines which examination must be performed, i.e. which imaging protocol with which parameter settings, and which results in the form of postprocessed medical images for the patient are required for a meaningful evaluation.

The indication information, together with the further factors, is typically specified manually by the medical personnel as part of the examination planning via a corresponding input unit or it is already available in a structured coded format for further use, e.g. in a hospital or radiology information system (HIS/RIS) and/or in an electronic health/medical record (EHR/EMR). Alternatively, the information may be present in unstructured form, e.g. in the form of a referral, previous image data and/or a previous evaluation report of the patient. The indication information and if applicable further factors can also be extracted here via known methods for natural language processing (NLP) or image analysis methods.

A proposal to utilize existing indication information for the purpose of automatically deriving control data records is specified in the European patent application EP 3451211 A1.

Provision is made here for applying an ontology such that data is converted into corresponding control data records for performing image capture, reconstruction and/or postprocessing steps, whereby manual inputs can be largely omitted.

SUMMARY

In practice, the automatically provided control data records must often be manually adapted subsequently, said adaptations being specific to a user and/or a medical facility or the region of the medical facility.

Solutions are known which link the individual postprocessing steps for the generated images to the selected imaging protocol, though this association is neither patient-specific nor user-specific.

Taking the foregoing as a starting point, an object of one or more embodiments of the present invention is to provide mechanisms and/or means which from the outset allow not only patient-specific automation of a medical imaging workflow but also user-specific and/or facility-specific automation of a medical imaging workflow. In particular, an object of one or more embodiments of the present invention is to further reduce the need for manual interaction between user and medical imaging installation.

At least this object is achieved by a method for controlling a medical imaging installation, a corresponding control unit, a medical imaging installation comprising the control unit, and a corresponding computer program product and a computer-readable medium as claimed in the independent claims. Preferred and/or alternative advantageous embodiment variants are specified in the dependent claims and the disclosure.

At least the above-mentioned object is inventively achieved as described below in respect of the claimed method and the claimed devices. Features, advantages or alternative embodiment variants cited in this context apply equally to the other claimed subject matter and vice versa. In other words, the claims in question (e.g. relating to a method) can also be developed with features that are described or claimed in connection with one of the devices. In this case, the corresponding functional features of the method are developed by the corresponding representational modules or units in question.

A first aspect relates to a method for controlling a medical imaging installation. The method is designed as a computer-implemented method, meaning that at least individual or even all steps of the method are executed by a computer or an arithmetic module or a control unit.

A further aspect of the present invention relates correspondingly to a control unit for controlling a medical imaging installation. The control unit is designed and configured in the form of, or as a component part of, a data processing unit, and comprises means for performing individual or all steps of the inventive method. In another example, the control unit is designed and configured in the form of, or as a component part of, a data processing unit, and is configured to perform individual or all steps of the inventive method.

A further aspect of the present invention relates to a controller to control a medical imaging installation, the controller comprising: a memory storing computer-executable instructions; and at least one processor configured to execute the computer-executable instructions to cause the controller to capture patient-specific indication data, capture at least one of at least one user-specific preference parameter or at least one facility-specific preference parameter, automatically determine a control data record based on the patient-specific indication data and the at least one of the at least one user-specific preference parameter or the at least one facility-specific preference parameter, and control the medical imaging installation based on the control data record.

The control unit comprises an interface unit which is designed to capture patient-specific indication data, and to capture at least one user-specific and/or facility-specific preference parameter via an interface unit, an arithmetic unit which is designed to automatically determine a control data record based on the indication data and the preference parameter, and to control the medical imaging installation using the determined control data record.

The inventive method comprises a plurality of corresponding steps.

A first step comprises the capture of patient-specific indication data via an interface unit.

A further step comprises the capture of at least one user-specific and/or facility-specific preference parameter via an interface unit.

A further step comprises the automatic determination of a control data record based on the indication data and the preference parameter via an arithmetic unit.

A further step comprises the control of the medical imaging installation using the determined control data record via an arithmetic unit.

A medical imaging installation comprising a control unit as described above forms a third aspect of embodiments of the present invention. A medical imaging installation is an imaging installation for use in the medical field. A medical imaging installation according to embodiments of the present invention uses e.g. x-radiation for the purpose of generating images and comprises e.g. at least one x-ray source and at least one x-ray detector. Alternatively, the medical imaging installation can use magnetic fields for the image data capture. In this respect, the medical imaging installation in embodiments of the present invention can be designed in the form of a C-arm device, a computed tomography system, a radiography device or a magnetic resonance tomography system. In further embodiments, the medical imaging installation can also use other image generation techniques such as e.g. ultrasound, positron-emission tomography, etc.

In embodiments, in addition to a unit for generating image data, the medical imaging installation also comprises a unit for inspecting, visually assessing or for evaluating the generated image data. In other words, the medical imaging installation provides e.g. a radiology workstation. In this case, the radiology workstation can be in an examination room directly adjacent to the unit for generating image data, in a neighboring control room and/or arranged remotely from the unit for generating image data, e.g. in a radiology department of the same medical facility, or in an independent radiology center which is physically separate from the medical facility. Both the unit for generating image data and the radiology workstation comprise operating units for a user, via which a human-machine interaction is realized. The operating units advantageously each comprise an interface unit which forms part of the control unit. An interface unit in this case comprises an output interface, e.g. in the form of a monitor. This is used in particular to display image data that has been generated. The interface unit further comprises an input unit for capturing a preference parameter and/or further input data for subsequent processing.

In embodiments, the control unit is also connected via corresponding data interfaces, which can also be included in the interface unit, to the medical imaging installation, in particular to the imaging components such as x-ray source or x-ray detector, for the purpose of data communication. Said data interfaces allow control information and/or captured image information to be transferred for subsequent processing. In embodiments, the control unit is integrated in the medical imaging installation. Alternatively, the control unit can also be arranged remotely or separately from the imaging components and even from the radiology workstation. The control unit is further designed to execute the steps for automatically determining a control data record based on the indication data and the preference parameter, and to control the medical imaging installation using the determined control data record. For this purpose, it comprises at least one arithmetic unit.

The control unit can be designed as a centralized or decentralized arithmetic unit or data processing unit or computer. The control unit can have one or more processors. The processors can be designed as a central processing unit (CPU) and/or as a graphics processing unit (GPU). Alternatively, the control unit can be implemented as a local or cloud-based processing server.

The interface unit be designed generally for the purpose of exchanging data between the control unit and further components of the medical imaging installation. The interface unit can also be used to exchange data between components of the control unit. The control unit can be implemented in the form of one or more individual interfaces, which can include e.g. a hardware and/or software interface, e.g. a PCI bus, a USB interface, a FireWire interface, a ZigBee interface or a Bluetooth interface. The interface unit can also have an interface to a communication network, said communication network being a Local Area Network (LAN), e.g. an intranet, or a Wide Area Network (WAN). The interface unit can have a LAN interface or a wireless LAN interface (WLAN or Wi-Fi) accordingly.

In embodiments of the present invention, the control unit can have e.g. a data storage entity which has a data connection to the arithmetic unit via the interface unit. In addition to other patient-specific data, e.g. indication data relating to a patient can be retrievably stored for the arithmetic unit in the data storage entity. Alternatively or additionally, lists comprising values for imaging, reconstruction and/or postprocessing parameters can also be retrievably stored in the data storage entity. The data storage entity can include previously defined assignments and/or relationships between indication parameters included in the indication data and values for imaging parameters, reconstruction parameters and/or postprocessing parameters. The data storage entity can be designed as a local storage entity of the medical imaging installation, e.g. as working memory or hard disk, or as a decentralized or centralized storage entity, e.g. an EHS system, hospital information system (HIS) or radiology information system (RIS) of a medical facility, e.g. a hospital. The data storage entity can also be part of a server system.

Step one of the method relates to the capture of patient-specific indication data. In this case, indication data is understood to be data which relates to a medical indication and concerns a patient, or a syndrome which a user/evaluator considers to be probable in the case of this patient. The indication data can also include details or information relating to a procedure to be carried out, in particular a medical imaging procedure. The indication data can be present in a structured format but also in unstructured format. In embodiments, the indication data can correspond to one of a plurality of known clinical conditions. In this case, a clinical condition designates an overall medical or anatomical status of the patient, said status being represented by the indication data. The interface unit can establish data communications with e.g. an HIS or RIS for the purpose of capturing the indication information. In embodiments, the indication data can also be retrieved from a modality worklist of the medical imaging installation via the interface unit. The modality worklist maps the indication data, which is present e.g. in an RIS terminology, directly onto DICOM attributes (DICOM=Digital Imaging and Communications in Medicine).

The indication data therefore represents prior knowledge relating to the patient. In some embodiments, the indication data may be present in free text format. In other embodiments, the indication data may correspond to an audio format, e.g. in the form of a dictated evaluation report on the patient. In such cases, the capture of the indication data can also include a semantic analysis or other method of natural language processing (NLP), so that the indication data in free text format is accessible to the arithmetic unit and can subsequently be processed by machine. The indication data can also be included in earlier medical image data of the patient to be examined. In embodiments, the capture of the indication data accordingly comprises an extraction of an evaluation or an evaluation for the patient via known image analysis methods.

In embodiments of the present invention, the indication data comprises one or a plurality of indication parameters, which considered together represent an indication for the patient.

Step two relates to the capture of at least one user-specific and/or facility-specific preference parameter. This step consequently comprises an interaction between user and control unit via the interface unit. The user can now enter a preference parameter via a haptic, acoustic and/or gesture-based interaction with the medical imaging installation. In this case, the preference parameter is specifically for the captured indication data concerning the patient to be examined. In this way, the preference parameter in embodiments characterizes a preferred setting or a preferred value for a parameter of a medical imaging protocol or for an image reconstruction or image postprocessing method. It is inventively characteristic of the preference parameter that it is user-specific and/or facility-specific. In practice, for comparable or identical indication data, different users prefer different imaging protocols, different values for individual or multiple protocol parameters, or different specifications for the image reconstruction or subsequent image processing for the evaluation. Furthermore, local or regional differences, i.e. facility-specific differences, can be observed in respect of administrating the treatment or examination of patients with identical results or similar indications or similar medical conditions, from the imaging through to the evaluation. This means that e.g. regional differences occur in the organization of standard image recording/imaging protocols for one and the same indication. As a result of this, imaging protocols considered as established are not available at certain facilities in other places, and vice versa. The inventive capture of the user-specific and/or facility-specific preference parameter advantageously allows these preferences/differences to be taken into consideration when determining the control data record associated with the indication data that has been captured. Embodiments of the present invention takes as a starting point that both a user-specific and/or a facility-specific preference parameter is captured by a user input. In embodiments, a user therefore also specifies preference parameters which are specific to the medical facility. In embodiments of the present invention, provision is made for capturing not just one but a plurality of preference parameters, e.g. two, three, four or more.

In embodiments of the present invention, the at least one preference parameter corresponds to a parameter for the image data capture via the medical imaging installation and/or for an image reconstruction from the captured image data and/or for a postprocessing of the reconstructed image data. In embodiments, the preference parameter therefore corresponds to a value specification for a protocol parameter of an imaging protocol, a reconstruction protocol or a postprocessing protocol. In embodiments of the present invention, the preference parameter is a parameter from the group comprising the following parameters: field of view, contrast medium, matrix size, dosage, reconstruction kernel, filtering, virtual native reconstruction, energy level for monoenergetic images, iodine map, rendering parameters, special segmentation.

Step three of the method relates to the automatic determination of a control data record based on the indication data and the preference parameter. The automatic determination comprises a machine-based, indication-specific assignment of control data to the indication data. In embodiments, the determined control data record comprises a (complete) set of value specifications for the protocol parameter of an image recording protocol. In further embodiments, the determined control data record comprises value specifications for reconstruction parameters of an image reconstruction algorithm. In further embodiments, it comprises value specifications for an image (post)processing algorithm which is applied to the reconstructed image data. In the context of the application, references to the individual parameters included in the control data record generally signify protocol parameters. In this respect, in embodiments of the method, the control data record comprises at least one control instruction relating to an image data capture via the medical imaging installation and/or relating to an image reconstruction from the captured image data and/or relating to a postprocessing of the reconstructed image data.

The automatic determination of these value specifications inventively no longer takes only the indication data into account but also the at least one preference parameter, so that in step three an assignment rule is applied which varies from a standard assignment between indication data and control data.

Therefore, embodiments of the present invention advantageously allows the automated modification of standardized image capture protocols, reconstruction protocols and/or processing protocols, and therefore the creation of novel image capture methods, reconstruction methods and/or processing methods which were not previously available.

Step four relates to the control of the medical imaging installation using the determined control data record, i.e. the execution of the control data. The determined control data record is therefore transferred from the arithmetic unit via the interface unit to at least one and preferably multiple components of the medical imaging installation, where it is executed in accordance with the value specifications contained therein for the protocol parameters. As a result, image data is captured, reconstructed and/or postprocessed on the basis of the value specifications of the determined control data record.

In embodiments of the present invention, the automatic determination comprises automatically selecting a control data record corresponding to the patient-specific indication data from a previously defined assignment between a plurality of different indication data and a plurality of different control data records. This approach does not initially take the captured preference parameter(s) into account, but uses already known, customary or previously defined assignments between indication data and the control data. A known assignment can be developed using an ontology or a control data library, e.g. as described in the European patent application EP 3451211 A1. There, the control data record is determined from a control data library in accordance with the indication data that is represented in the ontology. This determination takes place via inference (logical conclusions) and/or numeric modeling. Via inference, terms of the ontology (indication ontology) and the control data library are related to each other and logical conclusions are derived in order to determine the appropriate control data record. In the case of numeric modeling, the determination is effected using numerical methods. For given indication data, numerical models output numerical probabilities for control data records. Alternatively, e.g. the data storage entity mentioned above can comprise a previously specified assignment rule, similar to a database, between indication parameters of the indication data and control parameters which are contained in the control data, including corresponding protocol parameters for image data capture, reconstruction and/or image postprocessing. In embodiments, the previously specified assignment rule can be based on a manual specification by a user and/or an administrator. In embodiments, as part of the automatic determination, the arithmetic unit then compares the captured indication data parameter-by-parameter with the indication parameters in the database, and assigns the associated protocol parameter values.

In particular, these already known assignment rules correspond to generally applicable medical guidelines, which must be strictly observed at all times in the treatment/examination of a patient.

In this inventive method variant, the indication data is initially assigned standard control data records comprising protocol parameters for established and widely applied image data capture protocols, reconstruction protocols and postprocessing protocols.

In a development of this embodiment, in a subsequent step of the automatic determination, provision is made for adapting the automatic selection of a control data record on the basis of the at least one preference parameter. In other words, in this development, a user-related or facility-related preference for configuring an image data capture protocol, reconstruction protocol and postprocessing protocol is taken into account subsequently, specifically in that at least one of the previously assigned protocol parameters according to a standard protocol is adapted to the captured preference parameter.

This approach advantageously allows already known and widely applied standard protocols to be initially assigned to a captured indication, using automatic or manual methods which are likewise already known for the assignment.

In a further embodiment of the inventive method, the automatic determination of the control data record includes applying a trained function of the machine learning to the indication data. In other words, a control data record is automatically derived from the indication data containing the indication parameters, the indication data being used as input values for a trained function or trained algorithm of the machine learning.

Machine learning in the sense of embodiments of the present invention comprises a computer-implemented technique in which an algorithm recognizes patterns or regularities on the basis of existing data and, by applying these in relation to unknown new data, autonomously derives solutions. Autonomous solution finding requires a training phase in which an algorithm of the machine learning is applied to a known, defined and usually very large data pool in order to ascertain those rules or predictions which achieve a desired output or a desired result. The training can be designed as supervised or unsupervised training, value pairs in the form of input values and associated correct output values being presented to the algorithm in the first variant, whereas in the second variant the algorithm must adapt itself autonomously on the basis of the input values in such a way that it delivers the correct output values.

The function of the machine learning is most advantageously designed as an artificial neural network. An artificial neural network follows the structure of a biological neural network such as e.g. a human brain. An artificial neural network preferably comprises, between an input layer and an output layer, a plurality of further layers, each comprising at least one node. Each node in this case corresponds to a processing unit which is similar to a biological neuron. Nodes within a layer of the network can be connected via directed edges to nodes of other layers. The edges define the data flow within the network. Each node therefore represents an operation which is applied to the input data. Each node or each of its edges also has a weighting parameter (weighting). This weighting parameter defines the influence or the importance of the output of a node as an input value for a receiving node. In the training phase, which is preferably performed as supervised learning, the artificial neural network refers to the training data to 'learn' the weighting parameters for all nodes and edges, and adapts these until the output layer of the network supplies the correct output values.

In a particularly preferred embodiment, use is made of a so-called 'deep learning' algorithm, e.g. in the form of a 'convolutional neural network'. The trained function is therefore designed in particular to perform a classification, the set of indication parameters that has been entered and if applicable the preference parameter that has been entered being assigned a defined protocol parameter set comprising at least one (value for a) protocol parameter for image data capture, image reconstruction and/or image postprocessing. As an alternative to a convolutional neural network, it is also possible to use long short-term memory (LSTM) networks or recurrent neural networks (RNN) which, unlike those cited above, have reverse feedback loops within the hidden network layers.

According to the method, the trained function of the machine learning can be designed to first perform a standard assignment of control data to the captured indication data, corresponding to recognized and established protocols for imaging, reconstruction and/or image postprocessing. The trained function can be further designed to take the at least one preference parameter into account only in a next part-step, and to modify the standard control data according to the preference parameter. Specifically, the trained function can adapt at least one value specification for the set of protocol parameters, said value specification having been determined on the basis of the standard assignment, to the preference parameter.

Alternatively, the trained function can be designed to directly specify the user-specific and/or facility-specific protocol parameter set for the control data record. In comparison with previously described method variants, this inventive embodiment is suitable for the purpose of determining a control parameter particularly quickly and thereby clearly accelerating the medical process.

In embodiments of the present invention, the at least one captured preference parameter is therefore used as an input value for the trained function of the machine learning. In this case, the trained function of the machine learning assigns a suitable control data record comprising a protocol parameter set to the indication parameters and the preference parameter jointly. In other embodiments, the preference parameter is not used as an input value for the trained function, but instead acts as a control element for specifying/adapting the weightings of the individual nodes of the network in the context of a learning process of the network.

In an embodiment of the present invention, the trained function of the machine learning is a function that is specific to a user or comprises program sections specific to various users. In this embodiment, provision can be made for supplying a user ID for identifying various users as an input value to the trained function, in order to activate the user-specific program part. In an alternative embodiment, the trained function of the machine learning acts on the basis of the indication data and the preference parameter as input data, irrespective of the respective user.

The inventive approach is based on the knowledge that a trained function of the machine learning, as part of its training, establishes a fixed relationship between input values, here in the form of indication parameters specific to a patient and if applicable the preference parameter and a user ID, and output values in the form of corresponding protocol parameter records for the control data record. In this respect, embodiments of the present invention advantageously allow an automatic and individualized determination of a set of protocol parameters for image data capture, image reconstruction and/or image postprocessing, and the generation of a corresponding control data record.

In a preferred embodiment, the trained function is designed as a function which has been trained using training data comprising training input data in the form of a plurality of indication data and a plurality of preference parameters, and training output data in the form of a plurality of corresponding control data records. In embodiments of the present invention, the training input data also comprises a user ID. In this way, the trained function can from the outset learn about a relationship that is specific to a user or a facility between indication data and a control data record for image data capture, reconstruction and/or image postprocessing.

In this respect, it should be noted here that the capture of indication data and the capture of at least one and preferably a plurality of preference parameters need not be temporally correlated. In particular, provision is made for the at least one captured preference parameter from previously completed patient examinations to be used as a subset of the training input data. In embodiments of the present invention, the capture of the preference parameter therefore takes place (long) before a determination of a control data record. In other embodiments, the capture of the preference parameter first occurs in the context of correction loop and only after a determination of a control data record has taken place. This is described in greater detail further below.

According to a further embodiment of the inventive method, the training of the algorithm of the machine learning is designed as supervised learning, as explained in the introduction, and takes place on the basis of a plurality of pairs of indication parameters, each having an assigned control data record comprising a set of protocol parameters in each case. When at least one preference parameter is taken into account as part of the training input data, the inventive assignment becomes specific to user preferences or specific to a facility or a region. For the purpose of training the function of the machine learning, use is generally made of the error feedback (backpropagation) method which consists in feeding back a variance between actual output value and desired output value, this being known from the training data, to the artificial neural network for the purpose of adapting the individual node weightings. The training data used in each case is preferably based on a plurality of actual previous examinations of patients, or is alternatively at least partly generated artificially via simulation.

The inventive method can be used in a particularly flexible manner if the trained function is continuously updated on the basis of completed automatic determinations of a control data record. In other words, the trained function is designed as a continuous leaning (CL) system. In this embodiment, the trained function is able continuously to update an initial learning process via the training input data and the training output data, and therefore continuously to update the model for the assignment of control parameters in the form of protocol parameters for the image data capture, reconstruction and postprocessing. In order to achieve this, according to embodiments of the present invention, the captured preference parameters of recently performed examinations are continuously monitored and stored. For example, the captured preference parameters are stored in the data storage entity cited above as a set of second training input data for second training output data in the form of the assigned control data. At predefined intervals, e.g. after completion of one, two, three or more examinations, the trained function executes an update learning process, applying the second training input data and training output data, and adapts the weightings of individual nodes of the network to the second training input data and second training output data.

In an alternative embodiment, the trained function is designed as a continuous learning system which does not require an initial training phase. Following every examination, the system updates the applied assignment model, which is based mainly on manual inputs from the user at first. Following each performance of an examination, the training data record is updated and the assignment model adapted correspondingly. This approach allows the trained function to react automatically at any time to changes in relation to facility-specific or user-specific preferences. The trained function therefore supplies a particularly reliable result. Servicing overheads for the medical imaging installation as well as erroneous or undesired determinations of control data records are reduced in this way.

In particular when such continuous self-learning systems become operational, provision can inventively be made for the trained function to only ever consider a preselection of appropriate control data for an assignment in respect of defined indications, in order to avoid clinically erroneous imaging protocols, reconstructions and/or postprocessing as a result of theoretically possible associations between indication data and control data. This a priori knowledge can be provided to the trained function e.g. via corresponding parameterization.

In other words, in embodiments of the method, the updating of the trained function includes the possibility of specifying individual assignment rules of the trained function via the interface unit. In particular, the assignment rules can be specified manually be the user. However, the assignment rules can preferably also be provided automatically via a network. In embodiments, the assignment rules can be specified before becoming operational and/or specified subsequently or updated later during operation. In the context of embodiments of the present invention, assignment rules can be designed in such a way that e.g. the set of protocol parameters of a control data record complies with clinical guidelines in every case. This is relevant in particular when a clinical guideline has been updated but this knowledge is not yet applied at a medical facility. The assignment rule thus ensures compliance with the latest version of the clinical guideline. If indication data shows that e.g. a representation of the Ca scoring is required as part of the evaluation, a further assignment rule can ensure that a Ca scoring protocol must imperatively be executed for the purpose of imaging. Protocol parameters for imaging which do not correspond are thus excluded by the assignment rule from the outset.

This approach accelerates the training process, such that reliable operation of the trained function and consequently a reduction or even avoidance of user interaction can be achieved particularly quickly.

In a preferred embodiment of the method, the trained function comprises a frequency-based model which takes into account a frequency of values for the at least one captured preference parameter. This means that the trained function, particularly in the context of continuous learning, is designed to capture how often a specific preference parameter or a value for a preference parameter corresponding to a defined control specification for the image recording, reconstruction and/or image postprocessing was entered by a user. The trained function is additionally designed to execute or adapt the automated, model-based assignment rule in a frequency-based manner.

In order to allow the user to confirm or correct or adapt an automatically determined control data record, a further embodiment of the present invention provides a step in which the automatically determined control data record is output via an interface unit. The output preferably comprises a graphical output of the control data via a monitor of the interface unit. The output preferably comprises each individual value for each of the protocol parameters contained in the control data record. If the user determines that a value for one of the protocol parameters does not correspond to their wishes or to the administration of the medical facility, embodiments of the present invention can provide for the user to modify this protocol parameter via the interface unit. If the values of the protocol parameter have been determined correctly, the user can confirm this manually via the interface unit.

As a further aspect, embodiments of the present invention relate to a computer program product comprising a computer program which can be loaded directly into a storage entity of a control unit of a medical imaging installation, with program sections for executing individual or all steps of the method for controlling the medical imaging installation when the computer program is executed in the control unit.

As a further aspect, embodiments of the present invention also relate to a computer-readable medium on which are stored program sections that can be read in and executed by an arithmetic or control unit, in order to execute individual or all steps of the method for controlling the medical imaging installation when the program sections are executed by the arithmetic unit.

A computer program product can include software comprising source code which must subsequently be compiled and linked or merely interpreted, or executable software code which merely needs to be loaded into a data processing unit for the purpose of execution. By virtue of the computer program product, the method can be executed quickly, in an identically repeatable manner, and resiliently. The computer program product is configured in such a way that it can execute the inventive method steps via the arithmetic or data processing unit. In this case, the data processing unit must have the requirements such as e.g. a suitable working memory, a suitable processor, a suitable graphics card or a suitable logic unit, so that the respective method steps can be executed efficiently.

The computer program product is stored e.g. on a computer-readable medium or on a network or server, from where it can be loaded into the processor of the respective data processing unit. The server, storage entity or network can be connected directly to the data processing unit or designed as part thereof. In addition, control information of the computer program product can be stored on a computer-readable medium. The control information of the computer-readable medium can be designed in such a way that it performs a method according to embodiments of the present invention when the data medium is used in a data processing unit. Examples of computer-readable storage media include a DVD, a magnetic tape or a USB stick on which is stored electronically readable control information, in particular software. When this control information is read from the data medium and stored in a data processing unit, all inventive embodiment variants of the previously described method can be performed. Embodiments of the present invention can thus relate to said computer-readable medium likewise. The advantages of the proposed computer program product and the associated computer-readable media correspond essentially to the advantages of the proposed method.

BRIEF DESCRIPTION OF THE DRAWINGS

The properties, features and advantages of the present invention and the manner in which these are achieved become clearer and more understandable in the context of the following description of the exemplary embodiments, these being explained in greater detail with reference to the drawings. The present invention is not restricted to these exemplary embodiments by reason of this description. Identical components are denoted by identical reference signs in the various figures. The figures are not generally to scale.

DETAILED DESCRIPTION

Figure 1:
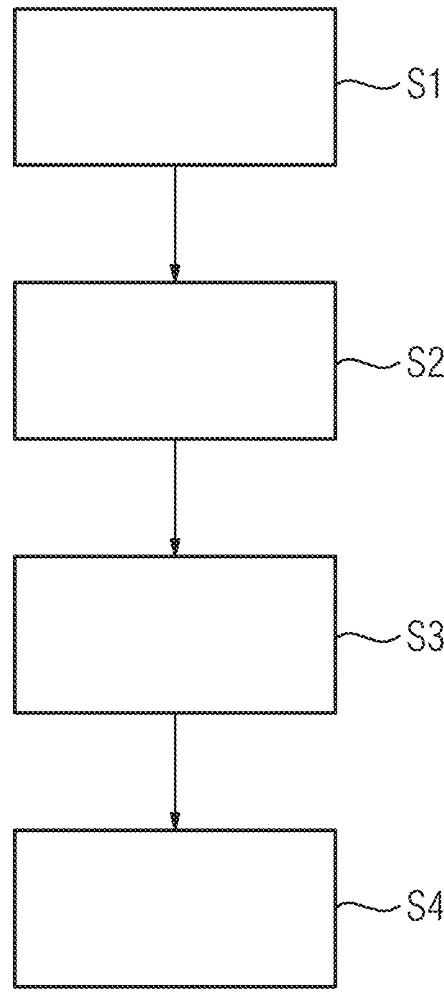
FIG. 1 shows a schematic illustration of the inventive method according to an exemplary embodiment of the present invention.

FIG. 1 shows a sequence diagram of an inventive computer-implemented method for controlling a medical imaging installation 1.

In step S1, patient-specific indication data is captured via an interface unit. The indication data can be extracted, provided or retrieved from various data sources, e.g. the indication data can be retrieved from a centralized or decentralized data storage entity, e.g. in the form of a patient database, e.g. from an RIS, HIS and/or PACS or from a cloud storage entity. An electronic health/medical record for each patient can be retrievably stored in the data storage entity, such that all of the available electronic documentation that could serve as indication data is consolidated at one (virtual) location. Alternatively, the electronic health/medical record can also be stored at least partly on the personal insurance card of the patient 3.

The indication data corresponds to prior knowledge about the patient 3. It comprises in particular details relating to a medical imaging procedure for the generation of image data for the patient 3, e.g. for the purpose of an evaluation. The indication data represents in particular an overall medical or anatomical status of the patient 3. The indication data can be present in a structured format but also in unstructured format. In this respect, step S1 can also comprise a structuring of the indication data, e.g. in order to make indication data in the form of free text accessible to the control unit 12 and allow subsequent processing by machine.

Step S1 optionally comprises the capture of supplementary information about the patient, e.g. anatomical or personal information. Such details can relate to e.g. the age, the gender or height and weight of the patient 3. This supplementary information can likewise be taken into account in step S3.

In step S2, at least one user-specific and/or facility-specific preference parameter is captured via an interface unit. The at least one preference parameter is therefore available for subsequent processing by the user, e.g. via display and input units 11, 7.

The preference parameter is specifically for the captured indication data relating to the patient to be examined. The preference parameter identifies a preferred setting or a preferred value for a parameter of a medical imaging protocol or for an image reconstruction or an image postprocessing method. The preference parameter is user-specific and/or facility-specific, and consequently allows preferences or differences to be taken into account when determining the control data record that is associated with the captured indication data. The at least one preference parameter is e.g. a parameter characterizing the field of view for the image data capture, a contrast medium that is used during the imaging, the matrix size, dosage, the reconstruction kernel or the filtering for a reconstruction algorithm. Preference parameters for image postprocessing can take the form of an instruction to perform a specific type of postprocessing, e.g. a virtual native reconstruction. A further example is the specification for an energy level of a monoenergetic image which is determined from the captured projection data. Other examples relate to an iodine map, rendering parameters or a specific segmentation.

In step S3, a control data record is automatically determined via an arithmetic unit 21 on the basis of the indication data and the preference parameter. In this case, the control data record comprises at least one control instruction corresponding to the at least one preference parameter, which control instruction relates to an image data capture via the medical imaging installation and/or to an image reconstruction from the captured image data and/or to a postprocessing of the reconstructed image data.

The automatic determination of the control data record comprises the application of a trained function of the machine learning to the indication data. Provision is therefore made in this step for determining a plurality of suitable control parameters for the indication data, said control parameters taking the form of individual protocol parameters for the purpose of image data capture, image reconstruction and/or image postprocessing. The trained function of the machine learning can be designed in the form of a neural network 400 in particular, as described further below with reference to FIG. 2.

In embodiments, step 3 can comprise continuously updating the trained function 400 on the basis of previous automatic determinations of a control data record. In other words, the trained function is designed as a continuously self-learning system. In order to achieve this, the arithmetic unit 21 can be designed to capture, save, and use for the purpose of updating the weightings of individual nodes of the neural network 400, preference parameters captured for recently executed examinations.

The neural network 400 can be adapted particularly well to local changes or to different/new users if the trained function comprises a frequency-based model which takes a frequency of values for the at least one captured preference parameter into account. If one value is entered more often than another for one and the same indication data via the preference parameter input, the neural network then learns via the update loop from the outset to assign the first of the two values for the control data record to the corresponding control parameter for future examinations. The second value is discarded or suppressed.

In this respect, according to embodiments of the present invention, the steps S1 to S4 can obviously be executed in a repeating loop (not shown) for a plurality of patients.

In embodiments, the updating of the trained function can also comprise manually specifying or adapting individual assignment rules of the trained function 400 via the interface unit. The neural network is configured at the same time in this way. In particular, via the assignment rules, control parameters that are clinically nonsensical for a patient 3 or undesirable for a facility or a user are excluded from the outset for specific indication data, i.e. specific medical conditions. In particular, it is possible via the assignment rules to ensure compliance with clinical guidelines. For this purpose, the assignment rules can be provided automatically via a network. The updating of the trained function 400 by adapting/specifying an assignment rule can take place in each execution of the iteratively executed method. In a further embodiment, the updating takes place e.g. after every five, eight or ten executions of the method.

Alternatively, for the purpose of determining the control data record via a function of the machine learning, provision can also be made for first preselecting, automatically and in a known manner, a control data record corresponding to the patient-specific indication data from a previously defined assignment between a plurality of different indication data and a plurality of different control data records, and only then adapting the automatic preselection of the control data record on the basis of the preference parameter. Here, the method first uses established methods for assigning control data records to the indication data, and then modifies these to the user preferences or facility specifications.

In an optional step S5 (not shown), provision can be made within the context of the method to output the automatically determined control data record via an interface unit, specifically via display unit 11, for the purpose of confirmation or adaptation by a user. In the event that despite the continuous self-learning the neural network has assigned at least one control parameter to the indication data in a manner which does not conform to the user or facility, the user is then able to enter a preference parameter corresponding to the control parameter via the input and correct it as desired before the control data record is executed.

Alternatively, the user can confirm the determined control data if this has been assigned as desired. A manual verification loop is thereby realized by the inventive method.

In step S4, the medical imaging installation 1 is controlled using the determined control data record via an arithmetic unit 21. In other words, in step S4, the determined control data record is sent at least partially to the recording unit 17 and/or the reconstruction and postprocessing unit 23 and is in each case executed there.

In summary, control data is automatically derived from clinical information (e.g. medical record, referral, preliminary evaluation) that is available for a patient 3, possibly supplementary information relating to the patient (=indication data), and user specifications or facility specifications (=preference parameters) that have been captured via appropriate interactive dialogs, said control data being not only specific to the respective patient but at the same time also taking into account user-specific and/or facility-specific preferences. This control data is used in a recording unit 17 or a reconstruction and postprocessing unit 23 of the medical imaging installation 1 for the purpose of image data acquisition, reconstruction or postprocessing. In order to process the indication data and the preference parameters, according to embodiments of the present invention, use is preferably made of methods from the field of artificial intelligence such as neural networks.

Figure 2:
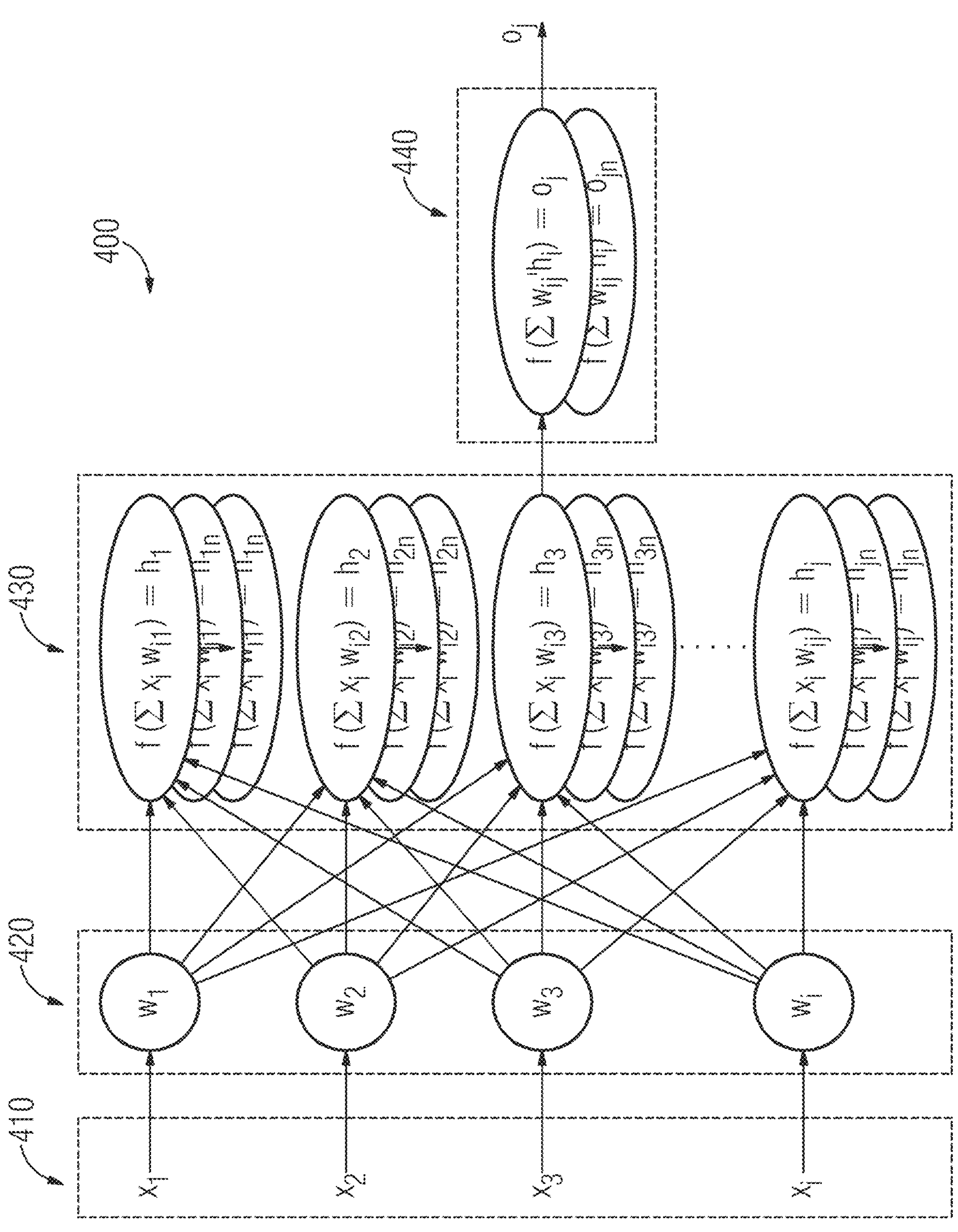
FIG. 2 shows a schematic illustration of a neural network for use in an inventive method.

FIG. 2 shows an artificial neural network 400 such as may be deployed in the method according to FIG. 1. The neural network 400 responds to input values from a plurality of input nodes xi 410, which are applied to generate one or more outputs oj. In this exemplary embodiment, the neural network 400 learns by adapting the weighting factors wi (weightings) of the individual node on the basis of training data. Possible input values of the input nodes xi 410 can comprise at least one or a plurality of preference parameters, e.g. in the form of indication data comprising a plurality of indication parameters. Input values can also be entered in the form of supplementary information relating to the patient, e.g. anatomical parameters of the patient such as e.g. weight, height, gender, etc. The neural network 400 is designed to weight the input values 410 on the basis of the learning process. The output values 440 of the neural network 400 preferably correspond to a plurality of protocol parameters for image data capture, image reconstruction and/or image postprocessing, said protocol parameters being incorporated as control parameters during the creation of a control data record. The output 440 can take place via a single output node oj or a plurality of output nodes oj. Alternatively, the neural network can be designed to transfer those protocol parameters assigned via a learning process to a control data record, e.g. in the last layer before the output layer, and to output said control data record as output values 440.

The artificial neural network 400 preferably includes a concealed layer 430 which comprises a plurality of nodes hj. A plurality of concealed layers hjn can be provided, a concealed layer 430 using output values from another concealed layer 430 as input values. The nodes of a concealed layer 430 carry out mathematical operations. An output value of a node hj corresponds in this case to a non-linear function f of its input values xi and the weighting factors wi. Following the receipt of input values xi, node hj performs a summation of a multiplication, weighted with the weighting factors wi, of each input value xi, e.g. as specified by the following function:

$$h_j = f\left(\sum_i x_i \cdot w_{ij}\right)$$

In particular, an output value of a node hj is formed as a function f of a node activation, e.g. a sigmoid function or a linear ramp function. The output values hj are transferred to the output node or output nodes oj. A summation of a weighted multiplication of each output value hj is again calculated as a function of the node activation f:

$$o_j = f\left(\sum_i h_i \cdot w'_{ij}\right)$$

The neural network 400 shown here is a feedforward neural network, in which all nodes 430 process the output values of a previous layer, in the form of their weighted sum, as input values. According to embodiments of the present invention, it is naturally also possible to deploy other types of neural network, e.g. feedback networks, in which an input value of a node hj can also be its output value at the same time.

The neural network 400 is trained to recognize patterns via a supervised learning method. One known approach is that of backpropagation, which can be applied for all exemplary embodiments of the present invention. During the training, the neural network 400 is applied to training input values in the form of a plurality of indication data, possibly a plurality of preference parameters and/or details for user identification, and has to generate corresponding previously known output values, the training output data, in the form of a plurality of corresponding control data records. Mean square errors (MSE) between calculated and expected output values are calculated iteratively, and individual weighting factors 420 are adapted until the variance between calculated and expected output values lies below a predefined threshold.

The neural network 400 here is designed as a continuously learning network which, even after the learning phase is complete, effects adaptations of the learned weighting factors wi for the plurality of nodes hj if the relationship between training input data and training output data changes over time.

Figure 3:
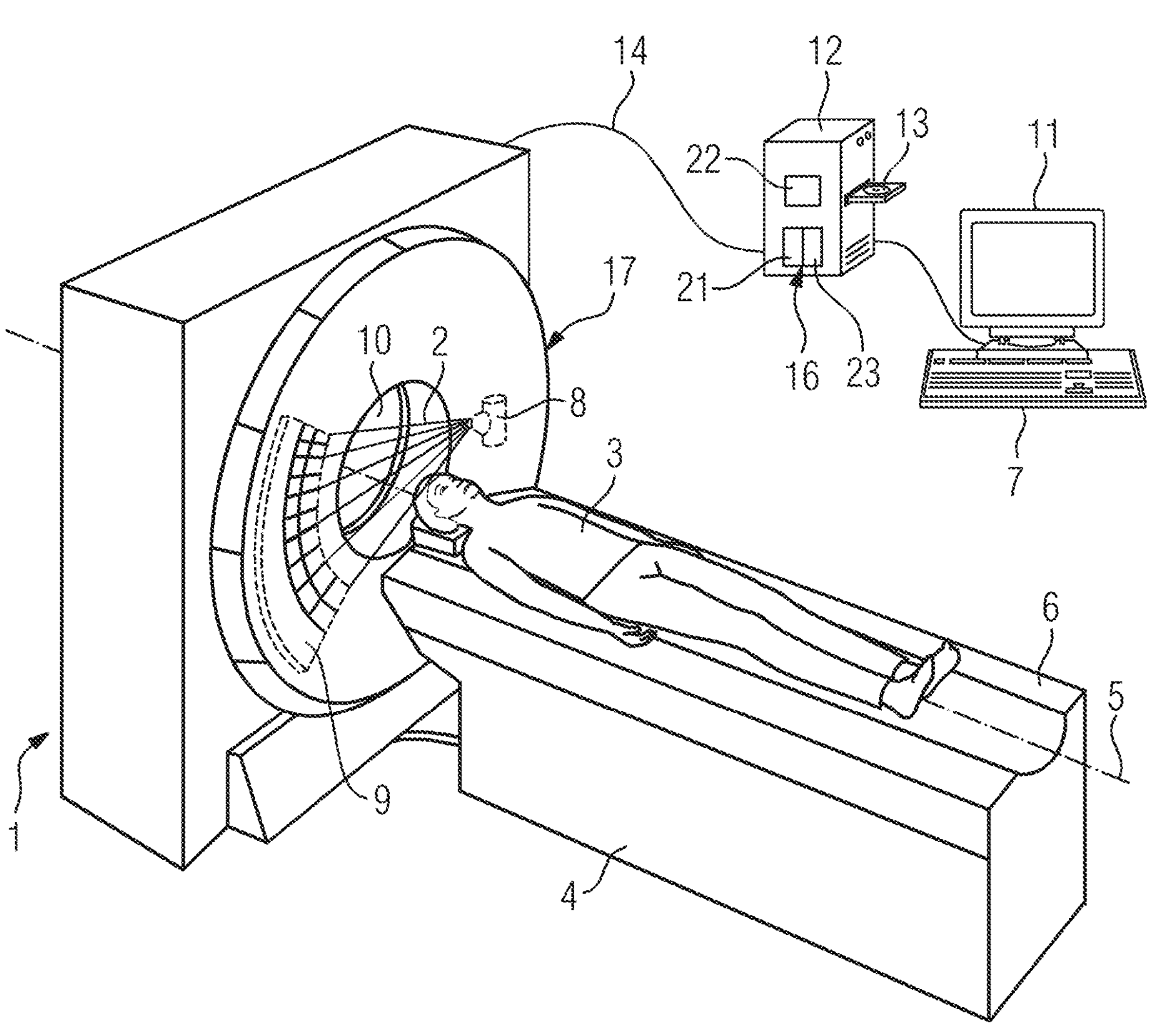
FIG. 3 shows a medical imaging installation in the form of a computed tomography system comprising an inventive control unit according to an exemplary embodiment of the present invention.

FIG. 3 shows a medical imaging installation 1 in the form of a computed tomography system 1. The computed tomography system 1 shown here has a recording unit 17 comprising an x-ray source 8 and an x-ray detector 9. For the purpose of generating image data, the recording unit 17 rotates about a system axis 5 in order to record x-ray projections, and during the recording the x-ray source 8 emits x-rays 2 which pass through the patient 3, are attenuated thus, and strike the x-ray detector 9. The settings that must be implemented, e.g. at the x-ray source 8, in order to generate the desired x-ray projection are defined by the protocol parameters of the desired imaging protocol. Protocol parameters for the image data capture are e.g. the x-ray energy or FOV information for mapping the desired body region of the patient.

The computed tomography system 1 has a control unit 12 in the form of a computer comprising an interface unit. The interface unit comprises a display unit 11, e.g. for the graphical display of medical image recordings at a radiology workstation of the medical imaging installation 1, here in the form of computed tomography recordings that are created from the x-ray projections via a reconstruction method or a control menu for the imaging installation 1. The interface unit also comprises an input unit 7 which is likewise part of the radiology workstation and is connected to the display unit 11. The display unit 11 can be e.g. an LCD, plasma or OLED screen. It can also be a touch-sensitive screen which also takes the form of input unit 7. Such a touch-sensitive screen can be integrated into the imaging device or designed as part of a mobile device. The input unit 7 is e.g. a keyboard, a mouse, a so-called "touch screen" or even a microphone for voice input. The input unit 7 can be configured to recognize movements of a user and translate these into corresponding instructions. The input unit 7 makes it possible, in particular via voice or keyboard, for e.g. a user to enter the at least one preference parameter, to specify individual assignment rules, or to confirm or adapt a determined control data record or individual protocol parameters contained therein.

The control unit 12 is connected to the rotatable recording unit 17 for the purpose of exchanging data. Firstly, the edge 14 is used e.g. to transfer control instructions from the control unit 12 to the recording unit 17, said control instructions relating to the data acquisition or image data capture, and in particular control parameters that have been determined in the form of protocol parameters and relate to e.g. x-ray dosage, rotation increments or similar are transferred via the edge 14. Secondly, projection data that has been recorded for the patient 3 for the purpose of image reconstruction via current reconstruction methods is transferred to the computer 12. The edge 14 is realized by wire-based or wireless device, mechanism and/or means in a known manner.

The control unit 12 comprises a data processing unit 16. This is configured to perform all of the arithmetic steps relating to the inventive method in order to determine a control data record in a user-specific and/or facility-specific manner on the basis of indication data and to control the medical imaging installation 1. The indication data and possibly further patient-specific details can be supplied to the image data processing unit 16 via the interface unit in a known manner, e.g. from a mobile known computer-readable data medium, a hospital or radiology information system (HIS or RIS) or via the internet, e.g. from a cloud storage entity or from an internal storage entity.

The data processing unit 16 comprises at least one processor, processing circuitry or means for executing the inventive method as described above with reference to FIGS. 1 and 2. The data processing unit 16 therefore comprises an arithmetic unit 21 for determining a control data record based on the indication data and the at least one captured preference parameter, using a trained algorithm of the machine learning. The arithmetic unit 21 here also comprises an assignment unit, which is configured to manage assignment rules that are defined in advance and can be adapted at any time by the user, and are then applied by the arithmetic unit 21 when determining the control data record. To this end, the assignment unit is likewise able to exchange data via the interface unit with e.g. the output and input unit 11, 7 in order to receive manual specifications, and/or with a local or centralized network unit which automatically sends signals (e.g. via push notifications) corresponding to an update of a clinical guideline to the assignment unit. Both units can be designed as separate processing units, but can also be designed as a single unit. At least the units 21 and 23 are connected via the interface unit, in order to provide the assignment rules to the arithmetic unit 21.

In addition to this, the image data processing unit 16 also comprises a reconstruction and postprocessing unit 23 which is designed to execute reconstruction and/or postprocessing steps in accordance with control instructions that are generated by the arithmetic unit 21 and contain control parameters in the form of protocol parameters for a reconstruction and/or postprocessing. A reconstruction of x-ray images from the captured projection data can be effected e.g. via a filtered back projection. Image postprocessing typically comprises subsequent processing of an image in a specific manner and/or a method of image analysis. For example, the image postprocessing can comprise a three-dimensional representation of the reconstructed image data, e.g. via volume rendering. The image postprocessing can also comprise specific tissue segmentation, e.g. for timorous tissue. A control instruction correspondingly comprises e.g. control parameters in the form of protocol parameters relating to the choice of filter kernel for the reconstruction, the rendering parameters or the pixel-based brightness threshold values for the segmentation.

The unit 23 is able to exchange data via the interface unit with the arithmetic unit 21 for the purpose of receiving the control instructions relating to an image reconstruction or image postprocessing, and with the display unit 11 for the purpose of displaying the reconstructed or postprocessed image data. The arithmetic unit 21 is also connected to the recording unit 17, likewise via the interface unit and edge 14, in order to transfer control instructions specifically for the image data capture.

The control unit 12 can communicate with the cited components or units in particular via the DICOM standard interchange protocol. Other communication protocols and data formats are also conceivable.

The control unit 12 can interact with a computer-readable data medium 13, in particular in order to perform a method according to embodiments of the present invention via a computer program comprising program code. Furthermore, the computer program can be retrievably stored on the machine-readable data medium. In particular, the machine-readable medium can be a CD, DVD, Blu-Ray disk, memory stick or hard disk. The control unit 12, and therefore its subcomponents, can be designed in the form of hardware or in the form of software. The control unit 12 is designed as e.g. a so-called FPGA (Field Programmable Gate Array) or comprises an arithmetic logic unit. The control unit 12, individual subcomponents or all subcomponents can be alternatively disposed in a decentralized manner, e.g. individual arithmetic steps of the method can be executed in a central data processing center of a medical services facility, e.g. a hospital, or in the cloud. In particular, data protection and patient privacy must be considered here in the context of data exchange. Alternatively, the control unit 12 can be designed entirely as a cloud-based computer, the data exchange with the imaging installation 1 taking place via a secure internet connection. In a preferred exemplary embodiment the communication is based on the DICOM standard, though other standards and data formats are likewise possible.

In the embodiment variant shown here, at least one computer program is stored in a storage entity 22 of the control unit 12, and performs all method steps of the inventive method when the computer program is executed on the computer 12. The computer program comprises program code for executing the method steps of the inventive method. The computer program can also be designed as an executable file and/or stored on a different data processing system than the computer 12. For example, the computed tomography system 1 can be configured in such a way that the computer 12 loads the computer program into its internal working memory via an intranet or the internet for the purpose of executing the inventive method.

Where not explicitly described but nonetheless applicable and within the meaning of the present invention, individual exemplary embodiments, individual part-aspects or individual features thereof, can be combined together or interchanged without thereby departing from the scope of the claimed invention. Advantages of the present invention that are described in relation to one exemplary embodiment are, where transferable, also applicable to other exemplary embodiments without this being cited explicitly.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A computer-implemented method for controlling a medical imaging installation, the computer-implemented method comprising:
  - capturing patient-specific indication data via an interface unit;
  - capturing, via the interface unit, at least one facility-specific preference parameter;
  - automatically determining, via an arithmetic unit and application of a trained neural network to the patient-specific indication data, a control data record based on the patient-specific indication data and the at least one facility-specific preference parameter, wherein
    - the trained neural network includes weighted nodes and has been trained using training input data and training output data, the training input data in the form of a plurality of indication data and a plurality of preference parameters, and the training output data in the form of a plurality of corresponding control data records,
    - the trained neural network is configured not to use the at least one facility-specific preference parameter as an input value and to use the at least one facility-specific preference parameter as a control element to specify or adapt weightings of individual ones of the weighted nodes,
    - the trained neural network is continuously updated based on completed automatic determinations of control data records,
    - updating of the trained neural network includes manually specifying individual assignment rules of the trained neural network via the interface unit, and
    - the trained neural network includes a frequency-based model that takes into account a frequency of values for the at least one facility-specific preference parameter; and
  - controlling, via the arithmetic unit, at least one of medical image data acquisition, medical image reconstruction or postprocessing of reconstructed medical image data by the medical imaging installation based on the control data record.

2. The method as claimed in claim 1, wherein the automatically determining comprises:
  - automatically selecting the control data record corresponding to the patient-specific indication data from a previously defined assignment between a plurality of different indication data and a plurality of different control data records.

3. The method as claimed in claim 2, wherein the automatically determining comprises:
  - adapting the automatically selecting of the control data record based on the at least one facility-specific preference parameter.

4. The method as claimed in claim 1, further comprising:
  - outputting the control data record via the interface unit for confirmation or adaptation by a user.

5. The method as claimed in claim 1, wherein the control data record comprises at least one control instruction relating to the at least one of the medical image data acquisition, the medical image reconstruction, or the postprocessing of the reconstructed medical image data.

6. The method as claimed in claim 1, wherein the at least one facility-specific preference parameter comprises a parameter for the at least one of the medical image data acquisition, the medical image reconstruction, or the postprocessing of the reconstructed medical image data.

7. A control unit for controlling a medical imaging installation, the control unit comprising:
  - an interface unit configured to
    - capture patient-specific indication data, and
    - capture at least one facility-specific preference parameter; and
  - an arithmetic unit configured to
    - automatically determine a control data record, via at least an application of a trained neural network to the patient-specific indication data, based on the patient-specific indication data and the at least one facility-specific preference parameter, wherein
      - the trained neural network includes weighted nodes and has been trained using training input data and training output data, the training input data in the form of a plurality of indication data and a plurality of preference parameters, and the training output data in the form of a plurality of corresponding control data records,
      - the trained neural network is configured not to use the at least one facility-specific preference parameter as an input value and to use the at least one facility-specific preference parameter as a control element to specify or adapt weightings of individual ones of the weighted nodes,
      - the trained neural network is continuously updated based on completed automatic determinations of control data records,
      - updating of the trained neural network includes manually specifying individual assignment rules of the trained neural network via the interface unit, and
      - the trained neural network includes a frequency-based model that takes into account a frequency of values for the at least one facility-specific preference parameter, and
    - control at least one of medical image data acquisition, medical image reconstruction or postprocessing of reconstructed medical image data by the medical imaging installation based on the control data record.

8. A medical imaging installation comprising a control unit as claimed in claim 7.

9. A non-transitory computer program product comprising a computer program configured to be loaded directly into a memory of a control unit of a medical imaging installation, the computer program including program sections for causing the control unit to execute the method as claimed in claim 1 when the computer program is executed in the control unit.

10. A non-transitory computer-readable medium storing program sections that, when executed by a control unit, cause the control unit to execute the method as claimed in claim 1.

11. A controller to control a medical imaging installation, the controller comprising:

a memory storing computer-executable instructions; and at least one processor configured to execute the computer-executable instructions to cause the controller to capture patient-specific indication data, capture at least one facility-specific preference parameter, automatically determine, via at least an application of a trained neural network to the patient-specific indication data, a control data record based on the patient-specific indication data and the at least one facility-specific preference parameter, wherein the trained neural network includes weighted nodes and has been trained using training input data and training output data, the training input data in the form of a plurality of indication data and a plurality of preference parameters, and the training output data in the form of a plurality of corresponding control data records, the trained neural network is configured not to use the at least one facility-specific preference parameter as an input value and to use the at least one facility-specific preference parameter as a control element to specify or adapt weightings of individual ones of the weighted nodes, the trained neural network is continuously updated based on completed automatic determinations of control data records, updating of the trained neural network includes manually specifying individual assignment rules of the trained neural network via an interface unit, and the trained neural network includes a frequency-based model that takes into account a frequency of values for the at least one facility-specific preference parameter, and control at least one of medical image data acquisition, medical image reconstruction or postprocessing of reconstructed medical image data by the medical imaging installation based on the control data record.

12. The computer-implemented method of claim 1, wherein the at least one facility-specific preference parameter includes at least one of a field of view, a reconstruction kernel, a dosage, a matrix size, a filtering specification, or a postprocessing type for the medical imaging installation, and the weighted nodes are organized in at least one concealed layer between an input layer and an output layer.

* * * * *